United States Patent [19]

Finlan et al.

[11] Patent Number: 5,047,213
[45] Date of Patent: Sep. 10, 1991

[54] BIOLOGICAL SENSORS

[75] Inventors: Martin F. Finlan, Aylesbury; Richard P. Harvey, Amersham, both of England

[73] Assignee: Amersham International PLC, Little Chalfont, England

[21] Appl. No.: 299,564

[22] Filed: Jan. 18, 1989

[30] Foreign Application Priority Data

Jan. 27, 1988 [GB] United Kingdom ................. 8801807

[51] Int. Cl.$^5$ ..................... G01N 21/00; G01N 21/55
[52] U.S. Cl. ............................. 422/82.11; 422/82.05; 422/57; 422/68.1; 422/58; 436/164; 356/318; 356/445
[58] Field of Search .......................... 422/82.05, 82.11; 356/318, 445

[56] References Cited

U.S. PATENT DOCUMENTS

| Re. 33,064 | 9/1989 | Carter et al. | 422/82.05 |
| 4,775,637 | 10/1988 | Sutherland et al. | 356/445 |
| 4,810,658 | 3/1989 | Shanks et al. | 422/82.11 |
| 4,877,747 | 10/1989 | Stewart | 422/82.11 |
| 4,909,990 | 3/1990 | Block et al. | 422/82.11 |
| 4,931,384 | 6/1990 | Layton et al. | 356/318 |

FOREIGN PATENT DOCUMENTS

| 0202021 | 11/1986 | European Pat. Off. | |
| 2174802 | 11/1986 | United Kingdom | |
| 2185308 | 7/1987 | United Kingdom | |
| 8807202 | 9/1988 | United Kingdom | 356/445 |

OTHER PUBLICATIONS

"Sensors and Actuators", vol. 4, pp. 299-304 (1983).

Primary Examiner—Robert J. Warden
Assistant Examiner—Theresa A. Trembley
Attorney, Agent, or Firm—Wenderoth, Lind & Ponack

[57] ABSTRACT

A biological sensor which utilizes the phenomenon of surface plasmon resonance to detect the refractive index change which occurs when two components—for example antibody and corresponding antigen—react with one another. Surface plasmon resonance takes place at the sloping exit surface of an optical waveguide such as a fiber optic 23. The input end of fiber optic 12 is connected to a light source 12. A layer 25 of metal is applied to the sloping exit surface so as to cause total internal reflection of the light proceeding down the fiber optic. Reflected light is detected by a detector 13. A sensitive, for example antibody, layer 26 is applied to the metal layer. Sample (not shown) reacts with layer 26 in such a way that the refractive index changes. Provided conditions are correct, this variation in refractive index can be monitored in detector 13 by virtue of the surface plasmon resonance which occurs in the area of total internal reflection.

15 Claims, 5 Drawing Sheets

BIOLOGICAL SENSORS

This invention relates to sensors for use in biological, biochemical and chemical testing and in particular to immunosensors used to monitor the interaction of antibodies with their corresponding antigens.

When antibodies are immobilized on a surface, the properties of the surface change when a solution containing a corresponding antigen is brought into contact with the surface to thus allow the antigen to bind with the antibody. In particular, the change in the optical properties of the surface can be monitored with suitable apparatus.

The phenomenon of surface plasmon resonance (SPR) can be used to detect minute changes in the refractive index of the surface as the reaction between the antigen and the antibody proceeds. Surface plasmon resonance is the oscillation of the plasma of free electrons which exists at a metal boundary. These oscillations are affected by the refractive index of the material adjacent the metal surface and it is this that forms the basis of the sensor mechanism. Surface plasmon resonance may be achieved by using the evanescent wave which is generated when a light beam is totally internally reflected at the boundary of a medium, e.g. glass, which has a high dielectric constant. A paper describing the technique has been published under the title "Surface plasmon resonance for gas detection and biosensing" by Lieberg, Nylander and Lundstrom in Sensors and Actuators, Vol. 4, page 299. Illustrated in FIG. 1 of the accompanying drawings is a diagram of the equipment described in this paper. A beam 1 of light is applied from a laser source (not shown) onto a surface 2 of a glass body 3. A detector (not shown) monitors the internally reflected beam 4. Applied to the external surface 2 of glass body 3 is a thin film 5 of metal, for example gold or silver, and applied to the film 5 is a further thin film 6 of organic material containing antibodies. A sample 7 containing antigen is brought into contact with the antibody film 6 to thus cause a reaction between the antigen and the antibody. If binding occurs the refractive index of the layer 6 will change owing to the increased size of the antibody molecules and this change can be detected and measured using the surface plasmon resonance technique, as will now be explained.

Surface plasmon resonance can be experimentally observed, in the arrangement of FIG. 1, by varying the angle of the incident beam 1 and monitoring the intensity of the internally reflected beam 4. At a certain angle of incidence the parallel components of the light momentum will match with the dispersion for surface plasmons at the opposite surface 8 of the metal film. Provided that the thickness of metal film 5 is chosen correctly there will be an electromagnetic coupling between the glass/metal interface at surface 2 and the metal/antibody interface at surface 8 which results in surface plasmon resonance and thus an attenuation in the reflected beam 4 at that particular angle of incidence. Thus, as the angle of incidence of beam 1 is varied, surface plasmon resonance is observed as a sharp dip in the intensity of the internally reflected beam 4 at a particular angle of incidence. The angle of incidence at which resonance occurs is affected by the refractive index of the material against the metal film 5—i.e. the antibody layer 6—and the angle of incidence corresponding to resonance is thus a direct measure of the state of the reaction between the antibody and the antigen. Increased sensitivity can be obtained by choosing an angle of incidence half way down the reflectance dip curve, where the response is substantially linear, at the beginning of the antibody/antigen reaction, and then maintaining that angle of incidence fixed and observing changes in the intensity of the reflected beam 4 with time.

Known systems of the type described with reference to FIG. 1 utilize a prism as the glass body 3. A diagram showing this arrangement is given in FIG. 2 which is simply an experimental set up intended to demonstrate surface plasmon resonance. The prism is shown under reference 8 and has applied to its undersurface a thin film 5 of metal. Light 1 from a laser source (not shown) is incident on the prism where it is refracted at point 9 before entering the prism. The internally reflected beam 4 is likewise refracted (at point 10) upon exiting from the prism.

One problem with the prism is that, as the angle of incidence is changed, either by moving the source, or rotating the prism, or both, the point on surface 2 at which the incoming beam is incident moves. Because of inevitable variations in the metal film 5 and the coating 6 of antibody, the angle of incidence which results in resonance changes as this movement occurs, which in turn introduces a further variable factor into the measurement and thus makes comparisons between the initial, unbound, state and the bound state of the antibody layer 6 less accurate. In addition to this, the system shown in FIG. 2 is not realistic for mass production, where cheap and readily disposable components are required.

According to the present invention there is provided a sensor for use in biological, biochemical or chemical testing, said sensor comprising an optical waveguide having an input end and an output end, a source of electromagnetic radiation whose output is applied to the input end of said optical waveguide, and wherein said output end of the optical waveguide is cut off at an angle to its axis to provide a sloping end face, means for monitoring the radiation from said source which is internally reflected at said face, a layer of metallic material applied to said sloping face, a layer of sensitive material applied to the metallic layer, and means for introducing onto the sensitive layer so as to react therewith a sample to be analysed, the arrangement being such that the radiation incident at said face of the optical waveguide causes surface plasmon resonance to occur, the characteristics of which resonance, as detected by said monitoring means, is dependent upon the reaction between the sample and the sensitive layer. Normally the radiation is in the visible or near-visible region, and this will be assumed throughout the present specification.

The term "optical waveguide" as used herein is intended to cover any transmission line for electromagnetic radiation within or near the optical range, and in which the wave propagates along the waveguide by means of repeated internal reflections off the wall of waveguide. Examples of such waveguides include the well-known fiber optic, on which the remainder of the present specification concentrates, but may also include rectangular section waveguides such as microscope slides along which, from edge to edge, light may be transmitted by means of repeated interval reflections off the major surfaces of the slide.

Fiber optics rely for transmission of light on repeated internal reflections at the walls of the fiber, the light taking a zig-zag course as it proceeds along the fiber. In order to ensure that such internal reflection takes place, fiber optics may be clad with a material having a lower refractive index than that of the material of the fiber. Commonly the fiber itself is made from glass, and the cladding of plastics material having a lower refractive index.

In order to mechanically support the fiber, it is preferred that the fiber be embedded in a block of transparent material. It is necessary that the material be transparent in order to allow it to pass light internally reflected at the sloping end of the fiber optic and which thus emerges from the fiber optic to be intercepted by the monitoring means. If the refractive index of the material of the block is chosen suitably, it can act in place of the cladding in ensuring internal reflections along the walls of the fiber optic. This can be useful where the integrity of the cladding is suspect, or where the cladding is not present at all.

The optics can be arranged in various different ways. For example, the radiation source may incorporate means for focussing the radiation (i.e. light) onto the input end face of the fiber optic. In these circumstances, the characteristics of the fiber optic are such that the sloping output face becomes illuminated with a range of angles of the input light. Thus the input beam effectively becomes several beams incident upon the glass/metal interface over a range of angles. The equipment can be chosen so that the range of angles spans the angle of dip corresponding to surface plasmon resonance. The corresponding internally reflected beam is likewise effectively several beams and may be monitored by a large area detector, or by an array of angularly spaced detectors positioned to collect the whole emergent beam. Thus the detectors can encode the information from the whole of the dip within milliseconds.

An equivalent effect can be obtained by arranging that the focussing means focusses the radiation onto the output surface of the fiber optic—in other words, onto the glass/metal interface. Here again the input beam effectively spans a range of input angles which can be simultaneously monitored as described above.

Although the layer applied to the metal film is assumed herein to be an antibody layer for use in immunoassays, it will be seen that any sensitive layer whose refractive index changes upon an event occurring can be used to thus provide a sensitive detector having a wide variety of applications in the fields of biology, biochemistry and chemistry. For example, the antibody could be replaced with other analyte specific binding entities such as DNA probes.

The metal film material is commonly silver or gold, usually applied by evaporation. The film needs to be as uniform as possible in order to cater for minute movement in the point of incidence of the incoming beam. It is assumed that a structured metal film will give the best resonance and there are various ways in which the glass body can be pretreated to improve the performance of the metal film and in particular to control the natural tendency of such films to form discontinuous islands:
1. Immersion in molten metal nitrates and other molten salts. This has the effect of introducing ions into the surface in a manner which can be structured and which can act as foci for island formation.
2. Ion bombardment of cold or hot glass to introduce nucleating sites. The removal of the more mobile ions has been demonstrated to reduce the thickness at which the evaporated film becomes continuous.
3. Electroless plating or electroplating over lightly evaporated films (0 to 100 angstroms thick). Electroless plated films survive to a greater thickness than evaporated films and could form more stable nuclei for subsequent coating.
4. Evaporating on to electroless plated films. The electroless plated films have a stronger tendency to an island structure and to bigger islands with greater spacing than evaporating films. This could be of advantage in tuning to light of a prescribed wavelength.

Coating performance can also be improved by:
1. Controlling the glass surface temperature during coating. Using a higher temperature substrate increases the islands' size and the spacing between them and conversely.
2. Evaporating in the presence of a magnetic or electrostatic field or electron emission device to control the ion content of the vapor stream. The state of charge of the substrate is known to affect the island structure.
3. Controlling the angle of incidence of the evaporated vapor stream relative to the glass surface. The mobility of the evaporated atoms and hence their ability to form bigger islands is greater when the momentum of the atoms relative to the glass surface is increased.

In order that the invention may be better understood, an embodiment thereof will now be described by way of example only and with reference to the accompanying drawings in which.

Figure 1:
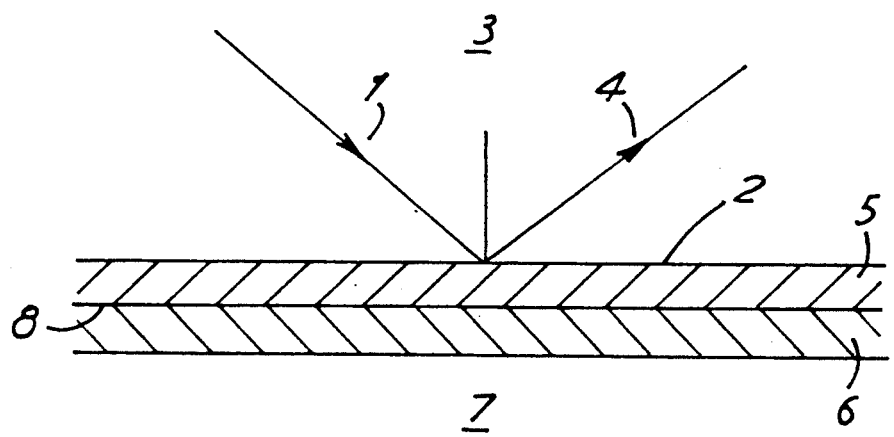
FIGS. 1 and 2 are diagrams of known experimental arrangements for demonstrating the surface plasmon resonance effect.
Figure 2:
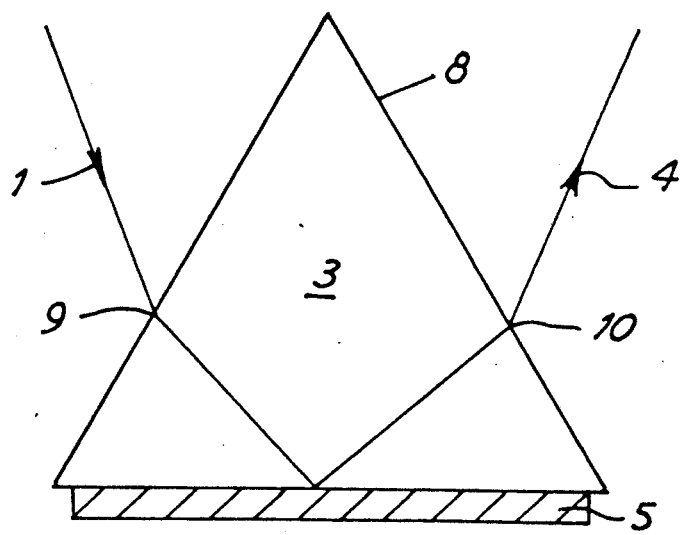
Figure 3:
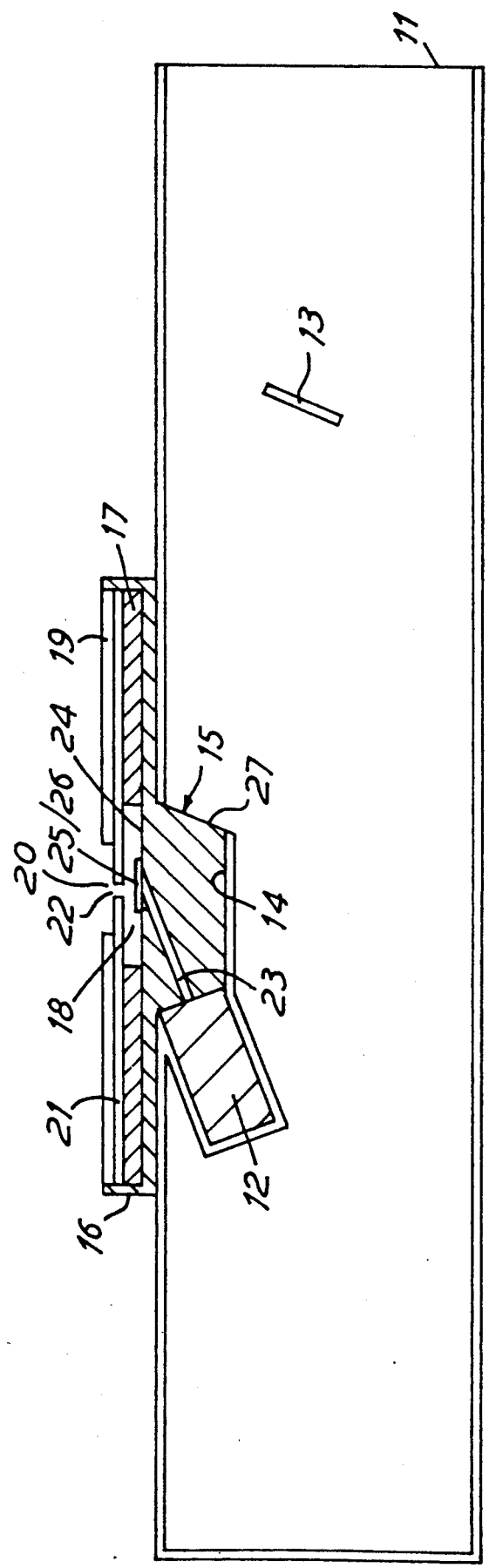
FIG. 3 is a diagrammatic side view of an embodiment of a sensor according to the present invention.

Referring to FIG. 3, the apparatus comprises a casing 11 carrying a laser diode and lens assembly 12 and a large area imaging detector 13 such as a diode array, charge couple device (ccd) or similar. The source produces a collimated input beam of electromagnetic radiation. The frequency of the radiation must be such as to result in the generation of surface plasmon waves and in practice will be within or near the visible region. Suitable sources include an infra red diode laser, but an ordinary light source, such as an LED (light emitting diode), with suitable filters and collimators, could be used.

The diode and lens assembly 12 is situated to one side of a well 14 formed in the top surface of the casing 11. This well is adapted to receive and locate a disposable test assembly built around a block 15 of radiation transparent material. The upper portion of the block is formed in the shape of a shallow tray having sides 16, and which contains three circular discs arranged one on top of another. The lowermost disc 17 is made of absorbent material and has a central through-aperture defining an active zone 18. The upper disc 19 has a central aperture intended to define a well 20 into which a sample to be tested is placed. The middle disc 21 has a central aperture 22 which is of a size to cause liquid in well 20 to travel through by capillary action into the active zone 18.

The lower portion of the block 15 is shaped to locate securely into the wall 14. The lower portion has cast or moulded therein a fiber optic 23 which extends from the output of the laser diode and lens assembly 12 to the surface 24. The output end of the fiber optic is cut off at an angle to define a sloping exit face which is substantially coplanar with the surface 24 of the block 15. This sloping exit face can be seen more clearly in FIGS. 4 and 5. The exit face is ground and polished for maximum accuracy.

The fiber optic is made of transparent material such as glass or plastics material which has a refractive index less than that of the surrounding block 15. Alternatively in the case of a clad fiber optic, the refractive index of the material of the block should be the same as or less than that of the cladding. If the cladding is suspect, a lower refractive index is best, as this ensures the internal reflections necessary for the light to travel along the fiber optic.

Applied to the sloping exit face of the fiber optic is a metal film layer 25, for example of silver, on top of which is applied a further layer 26 of a sensitive material whose refractive index changes as the test progresses. The sensitive layer 26 may for example be an antibody layer. The thickness of the metal layer 25 is such as to maximize the surface plasmon resonance reflectance dip when coated with the sensitive layer 26 and immersed in a typical test light from well 20—e.g. serum.

In order to reduce the effects of discontinuities in the layers 25 and 26, both of which can cause inaccuracies, it is desirable that the layers 25 and 26 are kept small in area, restricted in fact to the area of the sloping exit face of the fiber optic. The diameter of the fiber optic is typically 100 microns, but can span a large range of diameters depending on the application. Diameters less than 10 microns are not normally used because of increased difficulty in coupling light into the fiber optic. However, these smaller diameters could be used if special coupling techniques are employed, such as wedge or grating couplers.

As will be explained in more detail, during operation of the equipment, light from the laser diode and lens assembly is coupled into the fiber optic and is internally reflected at the sloping exit face to emerge from the fiber optic into the material of block 15, through which latter it travels before finally exiting through a window 27 in the well 14 to ultimately impinge on the sensitive area of the detector 13.

In order to use the apparatus a sample to be tester, containing an antigen capable of binding with the antibody molecules in layer 26 is placed in the well 20 and passes through apertures 22 by capillary action. Emerging from aperture 22, the liquid sample commences to flow radially outwards in all directions towards the absorbent disc 17, passing as it does so the antibody layer 26. The sample adjacent the layer 26 is thus being constantly replenished during the course of the test, which ensures maximum sensitivity.

As the sample flows past the layer 26 any antigen within the sample capable of binding with the antibody in layer 26 will do so, thus altering the refractive index of layer 26 as the reaction proceeds. This change in refractive index is continuously monitored during the test by directing along the fiber optic 23 the light beam from assembly 12. Provided that conditions are correct—in particular the angle of incidence at the point of incidence on the fiber optic exit face is correct—the application of the light will result in the generation of a plasmon wave, thus extracting energy from the input beam and causing an attenuation in the intensity of the output beam at a particular angle of incidence. The input beam is arranged such that the mid-angle of the range of angles of the input beam is approximately halfway down the reflectance dip, as described above, and the test is carried out at a constant angle of incidence, monitoring the intensity of the reflected beam above and below this mid point level. This gives a linear and highly sensitive output.

The initial reflectance dip which is chosen for setting up the angle of incidence should be the dip which results when some neutral or buffer solution is passed through the cell, or when the sample under test is passed through the cell but before any reaction thereof has taken place. In connection with the latter method, which is currently preferred, it is to be noted that, as sample begins to flow past the active zone adjacent layer 26 the refractive index does not start to change immediately due to the antibody/antigen reaction. There is thus sufficient time to take an initial reading with the unreacted sample flowing past, which reading can be utilized, using feedback circuitry, to rapidly adjust the angle of incidence to an appropriate value half way down the reflectance dip so that the rest of the test can be performed at this fixed angle.

With particular reference to FIGS. 4 to 7, we now consider three ways of optically operating the equipment. In the first way, shown in FIG. 4, the diode and lens assembly 12 is such as to provide an incident light beam 30 which is brought to a focus at the surface 24—i.e. on the sloping exit face of the fiber optic. The incident light beam thus covers a range of input angles which can be arranged to cover the angles of incidence which are known to produce the dip in the internally reflected beam, or to cover that part of the dip—for example just one side thereof—which is to be used for measurement.

Figure 4:
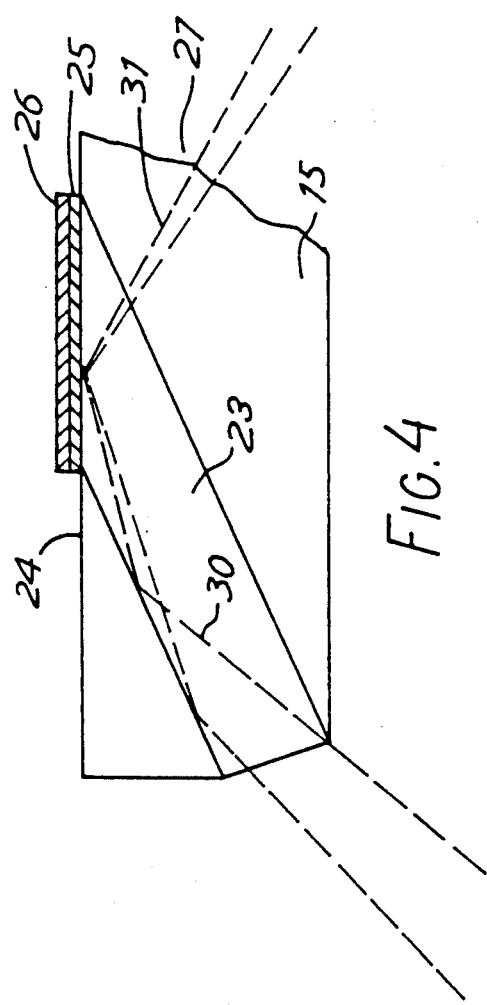
FIG. 4 is a diagrammatic side view of part of the sensor of FIG. 3, on a larger scale, showing an example of the path of the light rays.

The internally reflected beam, shown under reference 31, is divergent and escapes from the fiber optic due to its large angle of incidence with the wall of the fiber optic. After leaving the fiber optic the reflected beam travels through the cladding, if any, and then into the material of block 15. Due to the different refractive indices, there is bound to be some refraction of the beam, but this should be fairly minimal. Any such refraction can to a certain extent be compensated for as the reflected beam emerges from the block 15 into the air space within the casing 11. To this end the window 27 can be shaped such as shown in FIG. 4.

The reflected beam leaving window 27 is intercepted by the detector 13 which gives an output signal for analysis by external circuitry (not shown).

Figure 5:
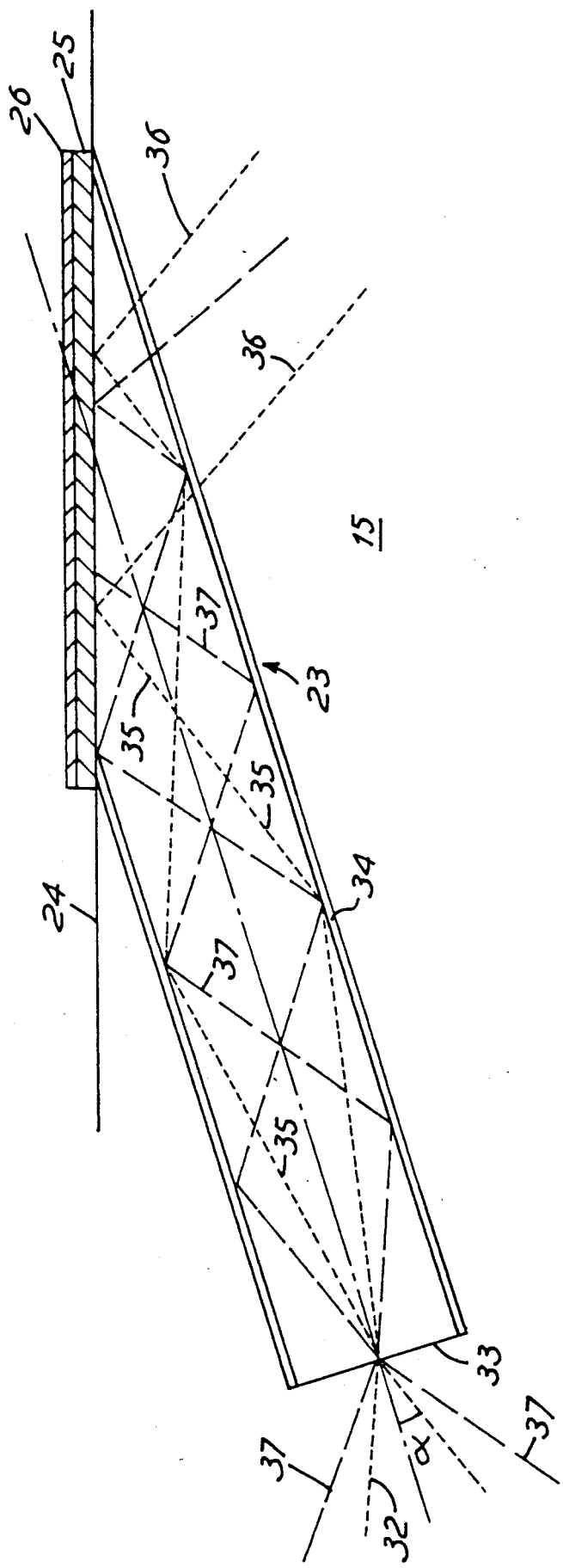
FIG. 5 is a diagrammatic side view of part of the sensor of FIG. 3, on a still larger scale, showing an alternative example of the path of the light rays.

In the alternative arrangement, shown in FIG. 5, the diode and lens assembly 13 is such as to provide a light beam 32 focussed onto the input face 33 of the fibre optic 23. FIG. 5 also shows, by way of illustration, the use of a clad fiber optic, the layer 34 of cladding being of a material having a lower refractive index than that of the fiber optic itself.

The dotted lines, reference 35, show the multiple reflection progress of the beam down the fiber optic until it reaches the sloping exit surface. Here, internal reflection takes place and an output beam 36 results. This latter beam passes through the cladding, then through the block 15 into the interior of the casing 11 where it is intercepted by the detector 13, as before.

The angle of the input beam is chosen to suit the circumstances; the dotted lines 37 represent the largest limit of the input angle beyond which internal reflection at the walls of the fiber optic will not take place, and transmission along the fiber optic is not possible.

Figure 7:
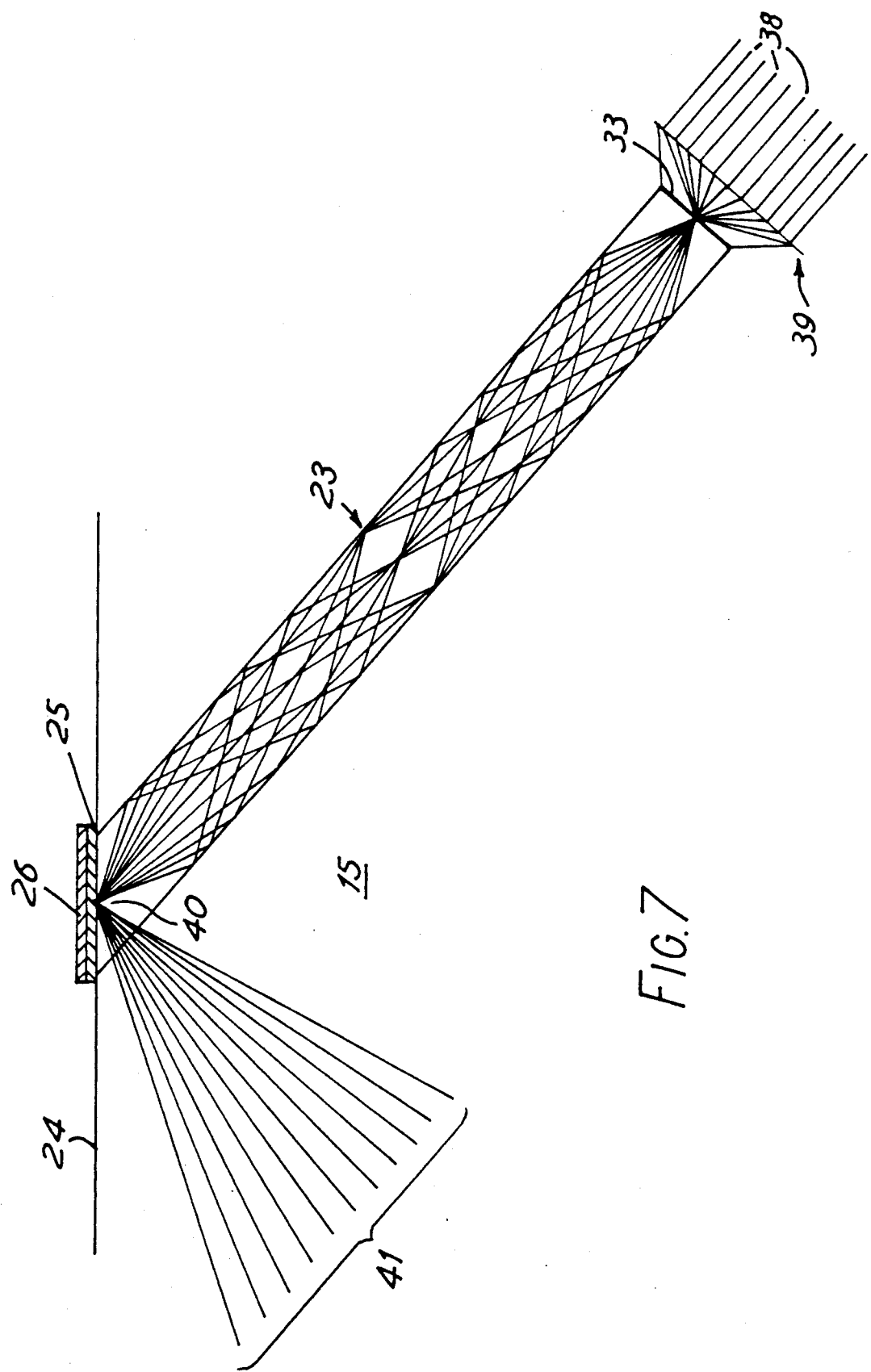
FIG. 7 is a view similar to FIG. 5, but illustrating the use of annular beams, such as in FIG. 6.

In a further alternative arrangement, shown in FIG. 7, the input light beam takes the form of a series of separate, spaced coaxial beams 38 of annular section. Such a composite beam can be produced, for example, by sputtering rings of obscuration, coaxial with a solid input light beam (not shown), onto a transparent plate (not shown) onto which the solid beam is incident at right angles.

Figure 6:
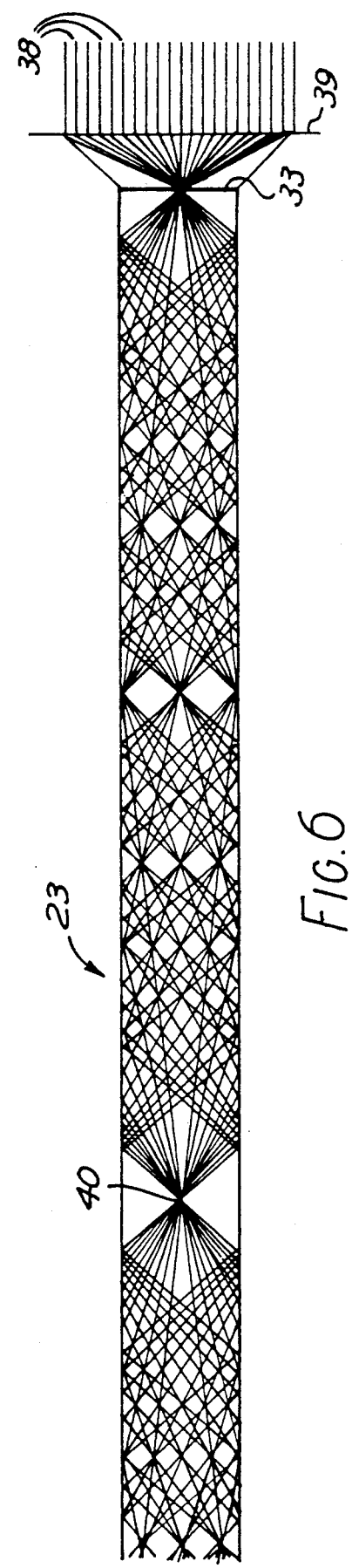
FIG. 6 is a diagrammatic side view showing the propagation of annular beams of light along a fiber optic.

Before discussing the FIG. 7 arrangement in detail, reference will be made of FIG. 6 which shows a diagram of the ray paths of a composite beam such as described above along a fibre optic 23. The composite beam is first brought to a focus at the input face 33 of the fiber optic by means of a suitable lens 39. For the fiber optic shown, lens 39 will be a circular lens, for planar optics (such as the above-mentioned microscope slide), a cylindrical lens will be used. The front face of the lens 39 is coated with emulsion in a pattern of concentric rings coaxial with the lens axis. This produces, from a solid input beam, a series of concentric coaxial ring-section beams—note that, for the sake of explanation, the input beam entering lens 39 is shown as already divided into separated ring-section beams. The number of rings of emulsion, and hence the number of separate annular beams generated, will be dictated by the required angular definition at the detector 13. In a typical arrangement, with a lens diameter of 2 cm and a fiber optic diameter of 1 mm, the number of rings would typically be 256.

As the light propagates into the material of the fiber optic it internally reflects off the fiber optic walls in the manner described above, and takes up a distinct pattern, as illustrated. In particular, it will be noted that, at a point 40 along the fiber optic, the separate beams making up the composite input beam come to a focus. Beyond the focal point 40, the ray pattern repeats itself and will thus result in further focal points (not shown) along the fiber optic length. The distance d of the first focal point 40 from the input face 33 is given by:

$$d = \frac{2 \times \text{diameter of fiber}}{\text{increment of gradient}}$$

Increment of gradient refers to the tangent of the angle of the incoming beam relative to the axis, converted into a gradient. For example, for a typical 10 micron diameter fiber at 0.001 gradient, the distance d is 20 mm. It will be seen that the exact distance d is dependent upon the number of separate annular input beams—the greater the number, the greater the distance.

In the arrangement of FIG. 7, the sloping exit face of the fiber optic is formed at such a position that it passes through the focal point 40 (or any of the later focal points, if a long fiber optic is required). The resultant divergent output beam 41 which passes into the block 15 is directed, as previously, to the detector 13.

The advantage of this arrangement is that, because at the point of internal reflection on the sloping exit face the incident beams are brought to a focus, the size of the active zone is kept to a minimum, thus reducing errors caused by irregularities in the layers 25 and 26.

In a further embodiment of the invention (not shown), the block 15 incorporates more than one fibre optic 23, each of these latter being illuminated with a common light source, or separate light sources. Each of these extra fiber optics terminate in a sloping exit face coplanar with surface 24 and spaced from adjacent fiber optics, and are covered with a metal layer 25 and sensitive layer 26, as before. It will be seen that, by this means, several distinct active areas can be defined, at each of which an analysis of a common sample can be carried out. As well as carrying out multiple tests simultaneously on one sample, this arrangement enables reference tests to be set up. Alternatively, by providing separate sample feeding arrangements—i.e. separate wells 20 etc.,—the same test can be carried out simultaneously on a number of different samples.

In a still further embodiment of the invention (not shown) the fiber optic is replaced by a plate of transparent material such as plastics or glass—a microscope slide will be suitable. One edge of the sheet is formed with said sloping exit face, and the light is inputted into the opposite edge. An advantage of using a sheet such as this is that multiple input beams can be applied to the input edge of the sheet and, if correctly adjusted, will propagate separately and independently along the sheet to the opposite edge. In conjunction with several distinct active areas, in the manner described above, this can enable simultaneous analysis of a number of different samples, or can enable a number of different tests (using, for example, different antibodies) to be carried out simultaneously on a common sample.

The use of the fiber optic to couple the light to the surface at which plasmon resonance takes place enables the area of the active zone to be minimized which reduces errors due to discontinuities in the metal and antibody films. In addition to this the physical size of the expensive antibody film is kept to a minimum. The system lends itself to mass production, and the fiber itself and its associated components should be cheap enough to be disposable, in the manner described above.

Although the fiber optic 23 is shown as being straight, there is no reason why a curved fiber optic could not be used if the physical constraints of the apparatus require it. For example, in a multiple-fiber apparatus where each fibre optic is illuminated with a separate light source, it may be found more convenient to use curved fiber optics from the (relatively large) light sources to the (relatively closely spaced) active zones.

The refractive indices of the block 15 and fibre 23 must be chosen with some regard to the quality of the surface plasmon resonance which results: in particular, we are looking for a steep slope on at least one side of resonance, or preferably on both sides since then the slopes can be algebraically added to give a higher amplitude output signal, and thus an improved signal to noise ratio. Generally speaking the refractive index of the fiber is chosen in relation to that of the sensitive layer 26 immersed in typical sample fluid to give a good resonance; the refractive index of block 15 is thence chosen in relation to that of the fiber to give the required optical properties.

We claim:
1. A sensor for use in biological, biochemical or chemical testing, said sensor comprising:
   an optical waveguide having an input end and an output end and along which radiation may propa- gate by means of internal reflections off its internal surfaces, a source of electromagnetic radiation whose output is applied to the input end of said optical waveguide, and wherein said output end of the optical waveguide is cut off at an angle to its axis to provide a sloping end face, wherein said radiation is input to the waveguide as a focussed beam so that the beam is incident at said end face as a spread of angles, and wherein the angle of the sloping end face is such as to (1) cause the incident beam to be totally internally reflected at said face, and (2) cause the thus-reflected beam to be incident on the wall of the waveguide at an angle sufficiently great for it to exit from the waveguide without being subject to further internal reflection, means for monitoring the radiation from said source which is internally reflected at said face, a layer of metallic material applied to said sloping face, a layer of sensitive material applied to the metallic layer, and means for introducing onto the sensitive layer so as to react therewith a sample to be analyzed, the arrangement being such that the aforesaid spread of radiation incident at said face of the optical waveguide is such as to include that angle at which surface plasmon resonance occurs, and allows the changing characteristics of the resonance to be monitored, which characteristics, as detected by said monitoring means, are dependent upon the reaction between the sample and the sensitive layer.

2. The sensor as claimed in claim 1 wherein said optical waveguide is formed of solid material transparent to the radiation in use, and along which the radiation propagates by means of internal reflections off its internal surfaces.

3. The sensor as claimed in claim 2 wherein the optical waveguide is a fiber optic.

4. The sensor as claimed in claim 2 wherein the optical waveguide is a rectangular slab of transparent material, such as a microscope slide.

5. The sensor as claimed in any one of claim 2 to 4 wherein the material of the waveguide is clad with a material having a refractive index which is lower than that of the waveguide material.

6. The sensor as claimed in any one of claim 2 to 5 wherein the material of the waveguide, and its cladding (if any) is embedded in a block of transparent material.

7. The sensor as claimed in claim 6 wherein the material of said block has a refractive index which is lower than that of the waveguide material.

8. The sensor as claimed in either one of claims 6 or 7 wherein said block is arranged to receive light internally reflected off said sloping end face and passing out of said waveguide medium, and wherein said block has an output face through which such internally reflected light passes, to be incident on said monitoring means.

9. The sensor as claimed in claim 8 wherein said output face is curved, having a center of curvature coincident with the point at which the radiation is incident on said end face.

10. The sensor as claimed in any one of claims 2 to 9 or a further including focussing means for focussing the radiation from the source onto the sloping end face.

11. The sensor as claimed in any one of claims 2 to 9 or 1 further including focussing means for focussing the radiation from said source onto the input of the optical waveguide.

12. The sensor as claimed in claim 11 wherein the optical waveguide is of circular cross-section, further including means for forming the radiation from the source into a series of separate radially spaced, coaxial beams of annular section.

13. The sensor as claimed in claim 11 wherein the optical waveguide is of rectangular cross section, further including means for forming the radiation from the source into a series of separate spaced planar beams.

14. The sensor as claimed in either one of claim 12 or 13 wherein the axial length of the optical waveguide is such that all of the separate input beams come to a common focus at the end face.

15. The sensor as claimed in any one of claims 2 to 14 or 1 including one or more further optical waveguides illuminated by a common source of radiation or by respective separate sources of radiation to enable testing of multiple analytes in a single sample, or multiple samples, to be carried out simultaneously.

* * * * *